United States Patent
Victor et al.

(10) Patent No.: US 10,772,553 B2
(45) Date of Patent: Sep. 15, 2020

(54) URINE SENSING OPTICAL FIBER PROBE AND SYSTEM FOR PERCUTANEOUS NEPHROSTOMY

(71) Applicant: TELEFLEX MEDICAL INCORPORATED, Morrisville, NC (US)

(72) Inventors: John C. Victor, Kunkletown, PA (US); Michael J. Morris, Jasper, GA (US); Mahmoud R. Shahriari, Tarpon Springs, FL (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 599 days.

(21) Appl. No.: 15/501,140

(22) PCT Filed: Aug. 7, 2015

(86) PCT No.: PCT/US2015/044166
§ 371 (c)(1),
(2) Date: Feb. 2, 2017

(87) PCT Pub. No.: WO2016/022894
PCT Pub. Date: Feb. 11, 2016

(65) Prior Publication Data
US 2017/0224266 A1    Aug. 10, 2017

Related U.S. Application Data

(60) Provisional application No. 62/034,317, filed on Aug. 7, 2014.

(51) Int. Cl.
*A61B 5/20* (2006.01)
*A61B 5/00* (2006.01)
*A61B 10/00* (2006.01)

(52) U.S. Cl.
CPC ............ *A61B 5/207* (2013.01); *A61B 5/0071* (2013.01); *A61B 5/0084* (2013.01); *A61B 5/20* (2013.01);
(Continued)

(58) Field of Classification Search
CPC ....... A61B 5/0071; A61B 5/0084; A61B 5/20; A61B 5/201; A61B 5/202; A61B 5/207; A61B 5/208; A61B 5/6874
See application file for complete search history.

(56) References Cited

U.S. PATENT DOCUMENTS 4,566,438 A * 1/1986 Liese ................... A61B 5/6848
600/129
5,280,788 A   1/1994 Janes et al.
(Continued)

OTHER PUBLICATIONS

K. Li et al., "Imaging Needle for Optical Coherence Tomography," Optics Letters, vol. 25, No. 20, Oct. 15, 2000, pp. 1520-1522.

*Primary Examiner* — Christopher A Flory
(74) *Attorney, Agent, or Firm* — BakerHostetler

(57) ABSTRACT

The present application describes a urine sensing probe and a system for detecting urine. The urine sensing probe includes a needle having a tubular portion and one or more optical fibers positioned within the needle. The one or more optical fibers have a distal surface that is oriented towards a beveled distal section of the needle and is oriented to one of its lateral sides. The distal surface of the one or more optical fibers ranges from about 90 to a critical angle with respect to a vertical axis of the needle. The present application also describes a system for sensing urine including a urine sensing probe.

20 Claims, 13 Drawing Sheets

(52) U.S. Cl.
CPC .............. *A61B 5/201* (2013.01); *A61B 5/202* (2013.01); *A61B 5/6848* (2013.01); *A61B 5/6874* (2013.01); *A61B 10/007* (2013.01)

(56) References Cited

U.S. PATENT DOCUMENTS

| | | | |
|---|---|---|---|
| 6,056,699 A | | 5/2000 | Sohn et al. |
| 2001/0012429 A1* | | 8/2001 | Wach .................. A61B 5/14546 |
| | | | 385/115 |
| 2003/0045798 A1* | | 3/2003 | Hular ................... A61B 5/0066 |
| | | | 600/476 |
| 2004/0010204 A1* | | 1/2004 | Weber .................. A61B 5/0084 |
| | | | 600/547 |
| 2004/0197771 A1 | | 10/2004 | Powers et al. |
| 2005/0261568 A1* | | 11/2005 | Hular ................... A61B 5/0066 |
| | | | 600/407 |
| 2008/0306391 A1* | | 12/2008 | Hular ................... A61B 5/0066 |
| | | | 600/478 |
| 2011/0060229 A1 | | 3/2011 | Hulvershorn et al. |
| 2011/0092823 A1* | | 4/2011 | Tearney ............... A61B 5/0066 |
| | | | 600/476 |
| 2011/0184259 A1 | | 7/2011 | Alarcon et al. |
| 2013/0310643 A1* | | 11/2013 | Gora ..................... A61B 1/041 |
| | | | 600/109 |
| 2014/0303494 A1* | | 10/2014 | Janicki ................... H01L 28/40 |
| | | | 600/424 |

\* cited by examiner

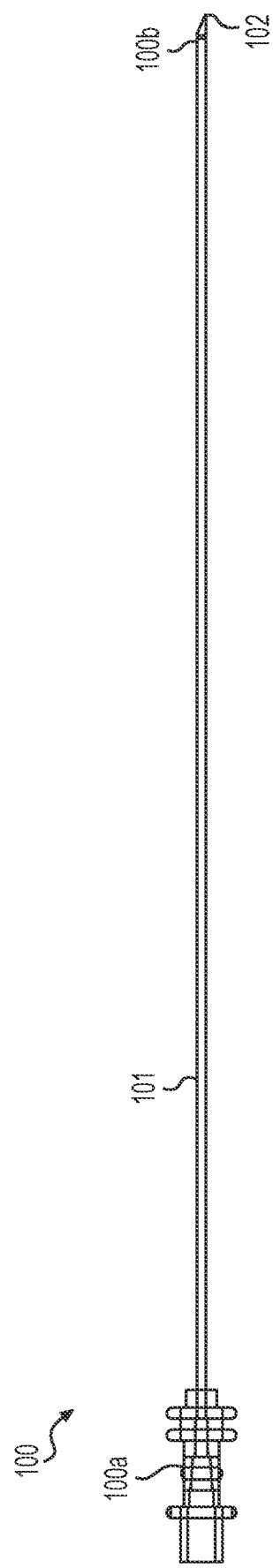
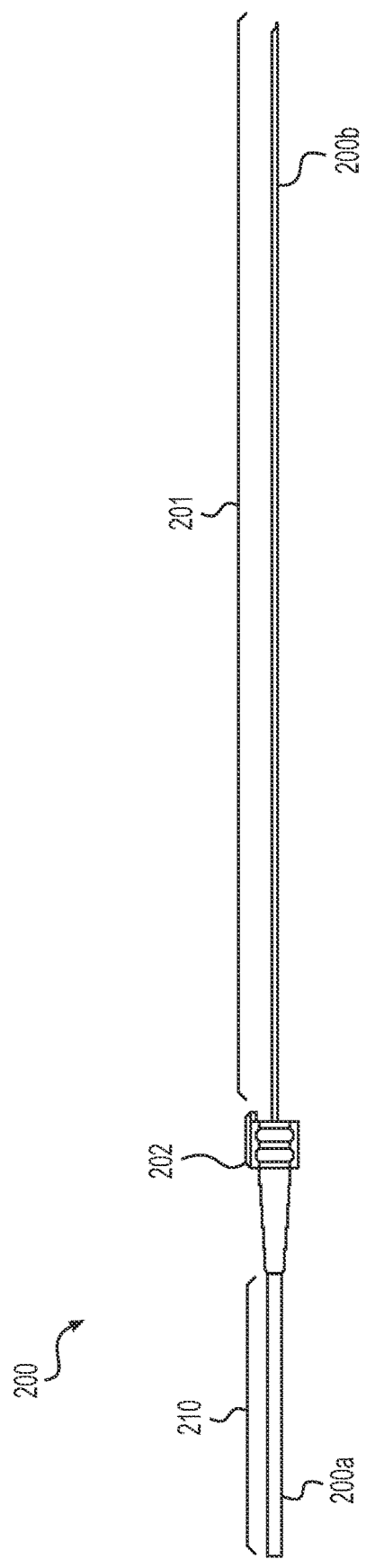
FIG. 1
FIG. 2

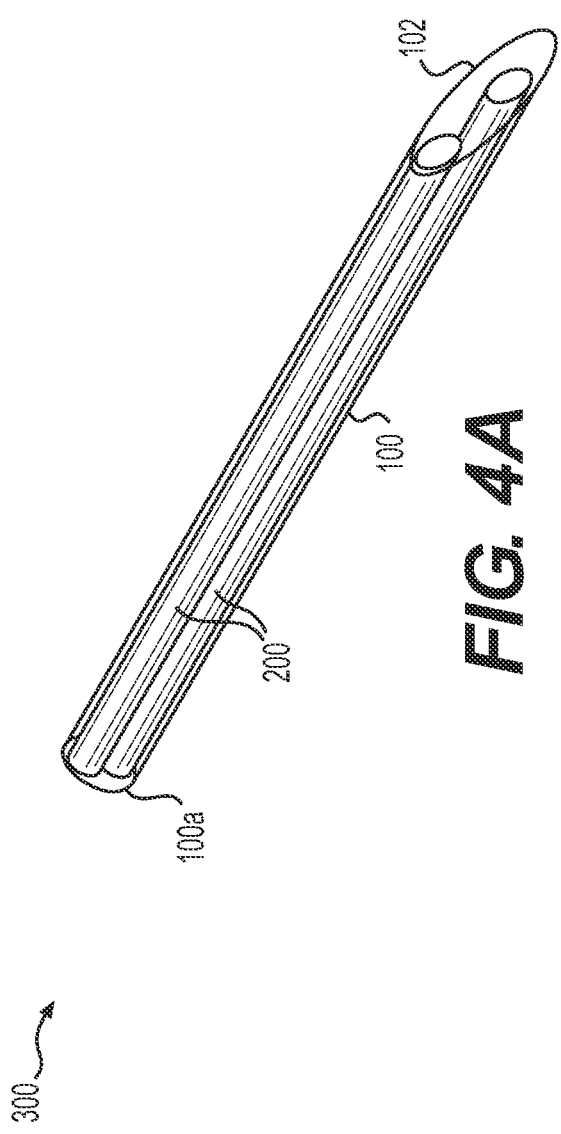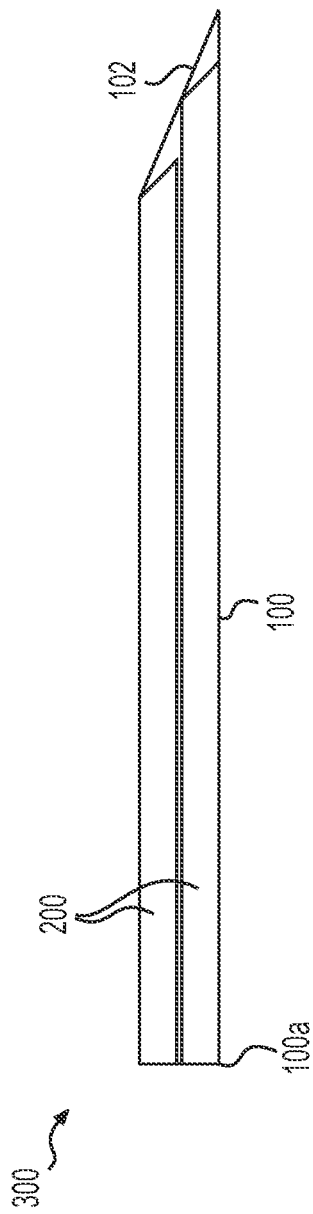

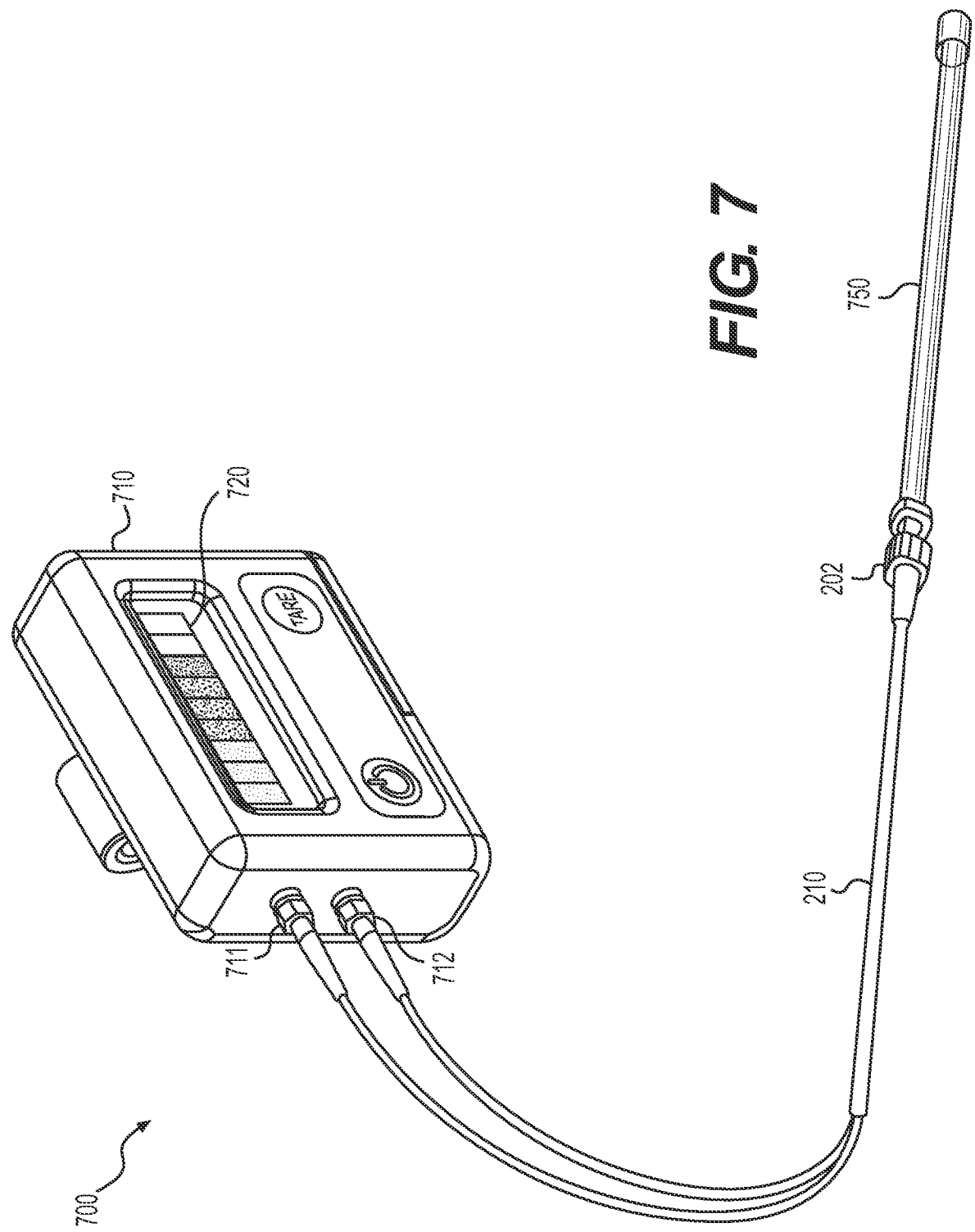

URINE SENSING OPTICAL FIBER PROBE AND SYSTEM FOR PERCUTANEOUS NEPHROSTOMY

FIELD

The present application generally relates to an apparatus and system for detecting and measuring fluorescence characteristics that are present in urine. More specifically, the present application includes a urine sensing probe used in combination with a user interface to excite urine with optical energy and detect optical emission characteristics thereof.

BACKGROUND

Percutaneous nephrostomy is generally understood to be an interventional procedure that is primarily used in the decompression of the renal collecting system. Generally, patients exhibiting symptoms associated with ureteral obstruction or congested kidneys are provided relief by placing a non-coring needle and stylet through the body wall into the renal saddle region of the suspect kidney.

At the time of tube placement, the cause of obstruction may not be known. When accurately placed, the stylet can be removed and urine aspirated from the needle. Following the alleviation of the congested state, the needle may also be used for the placement of stone removal devices and/or guide wires for stent placement.

Complications may occur while attempting to locate urine during a nephrostomy procedure. In fact, most percutaneous placements are achieved blindly without the aid of ultrasound or fluoroscopic guidance. For example, imprecise positioning may affect nearby structures ultimately affecting the surgical result.

What is therefore desired in the art is an improved apparatus and system for detecting the presence and location of urine inside the body.

What is also desired in the art is an apparatus and system capable of differentiating between urine in a congested kidney or obstructed ureter and urine present in other locations in the body.

What is also desired in the art is a method for detecting concentration of urine in-vivo to assess for certain risks.

SUMMARY

The foregoing needs are met, to a great extent, by the present application, by a urine sensing probe and system for detecting characteristics of urine.

One aspect of the present application advantageously provides a urine sensing probe including a needle and one or more optical fibers. The needle has a tubular portion, a proximal end, a distal end, and a beveled distal section. The beveled distal section is oriented towards a first lateral side of the needle. The one or more optical fibers are positioned within the needle. Each optical fiber has a distal surface that is proximate to the beveled distal section. The distal section preferably is oriented towards the first lateral side. The distal surface has an angle ranging from about 90° to a critical angle measured from a longitudinal or vertical axis of the needle.

Another aspect of the present application is directed to a urine sensing probe including a needle and an optical fiber. The needle has a tubular portion, a proximal end, a distal end, and a beveled distal section oriented toward a first lateral side of the needle. The optical fiber has a distal surface proximate to the beveled distal section and oriented towards the first lateral side. A portion of the distal surface is substantially parallel to the beveled distal section.

Another aspect of the present application advantageously is directed to a system for detecting urine in-vivo. The system includes a urine sensing probe, such as either of the above-mentioned urine sensing probes. The system also includes a source for transmitting excitation energy through the urine sensing probe towards urine. The system also includes a detector for detecting fluorescence in urine through the urine sensing probe.

There has thus been outlined, rather broadly, certain embodiments of the application in order that the detailed description thereof may be better understood, and in order that the present contribution to the art may be better appreciated. There are, of course, additional embodiments of the application that will be described below and which will form the subject matter of the claims appended hereto.

In this respect, before explaining at least one embodiment of the application in detail, it is to be understood that the application is not limited in its application to the details of construction and to the arrangements of the components set forth in the following description or illustrated in the drawings. The application is capable of embodiments in addition to those described and of being practiced and carried out in various ways. Also, the phraseology and terminology employed herein, as well as the Abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present application. Therefore, the claims shall be regarded as including such equivalent constructions insofar as they do not depart from the spirit and scope of the present application.

BRIEF DESCRIPTION OF THE DRAWINGS

FIG. 1 illustrates a needle according to an embodiment of the present application.

FIG. 2 illustrates an optical fiber according to another embodiment of the present application.

FIGS. 4A-B illustrate alternative views of FIG. 3A.

FIG. 7 illustrates a system for detecting urine according to an embodiment of the present application.

DETAILED DESCRIPTION

Figure 3A:
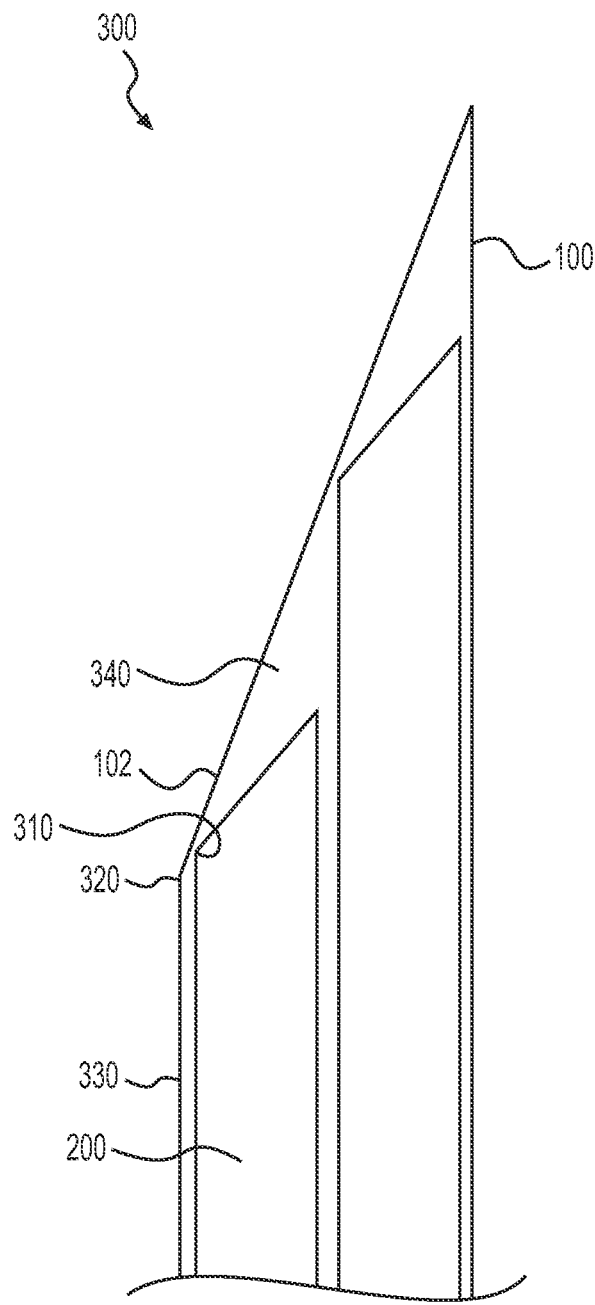
FIGS. 3A-E illustrate one or more optical fibers housed in a needle according to an embodiment of the present application.

The application will now be described with reference to the illustrated figures, in which like reference numerals refer to like parts throughout. Moreover, reference elements having the same last two digits are intended to reference similar elements. The drawings should not be construed as limiting the application. The drawings are intended only to be illustrative.

Reference in this specification to "one embodiment," "an embodiment," "one or more embodiments, or the like means that a particular feature, structure, or characteristic described in connection with the embodiment is included in at least one embodiment of the disclosure. Moreover, the term "embodiment" in various places in the specification is not necessarily referring to the same embodiment. That is, various features are described which may be exhibited by some embodiments and not by the other.

The many features and advantages of the application are apparent from the detailed specification, and thus, it is intended by the appended claims to cover all such features and advantages of the application which fall within the true spirit and scope of the application. Further, since numerous modifications and variations will readily occur to those skilled in the art, it is not desired to limit the application to the exact construction and operation illustrated and described, and accordingly, all suitable modifications and equivalents may be resorted to, falling within the scope of the application.

According to one aspect of the application, a urine sensing probe is described for sensing fluorescence characteristics in urine. In particular, the probe is configured to detect the presence of natural fluorophores present in urine that are excited by predetermined wavelengths of light.

In one embodiment, the probe includes a needle 100 as shown in FIG. 1, for example, including a tubular portion 101. The needle 100 includes a proximal end 100a, a distal end 100b and a beveled section 102. In particular, the beveled section 102 is oriented towards a first lateral side of the needle 100. In an embodiment, the beveled section 102 is less than about 25° with respect to an axial plane, e.g., vertical axis, of the needle. In an exemplary embodiment, the beveled section 102 is about 22° with respect to an axial plane, e.g., vertical axis, of the needle.

The needle preferably is made of stainless steel. Moreover, in one embodiment, the needle preferably is about 15 cm in length. The length of needle is constructed such that is is long enough to reach the renal saddle and/or ureter.

The urine sensing probe may also include one or more optical fibers. An optical fiber 200 is illustrated in FIG. 2. The optical fiber may include a polished distal surface. The optical fiber 200 includes a proximal end 200a and a distal end 200b. An mechanically robust fiber section 202 is disposed on the optical fiber 200. The mechanically robust optical fiber section 202 generally segregates an extension fiber section 210 of the optical fiber 200 from the elongate section 201 of the optical fiber that ultimately is positioned within the needle 100.

As shown in FIG. 2, an elongate portion 201 extends from the mechanically robust fiber section 202 to the distal end 200b of the optical fiber proximate a beveled section 102 of a needle as shown in FIG. 1. Another end of the the optical fiber (not shown) extends from an opposite end of the extension fiber 210 to an excitation source and/or emission sensor. The emission sensor and/or excitation source will be discussed in more detail below.

Figure 3B:
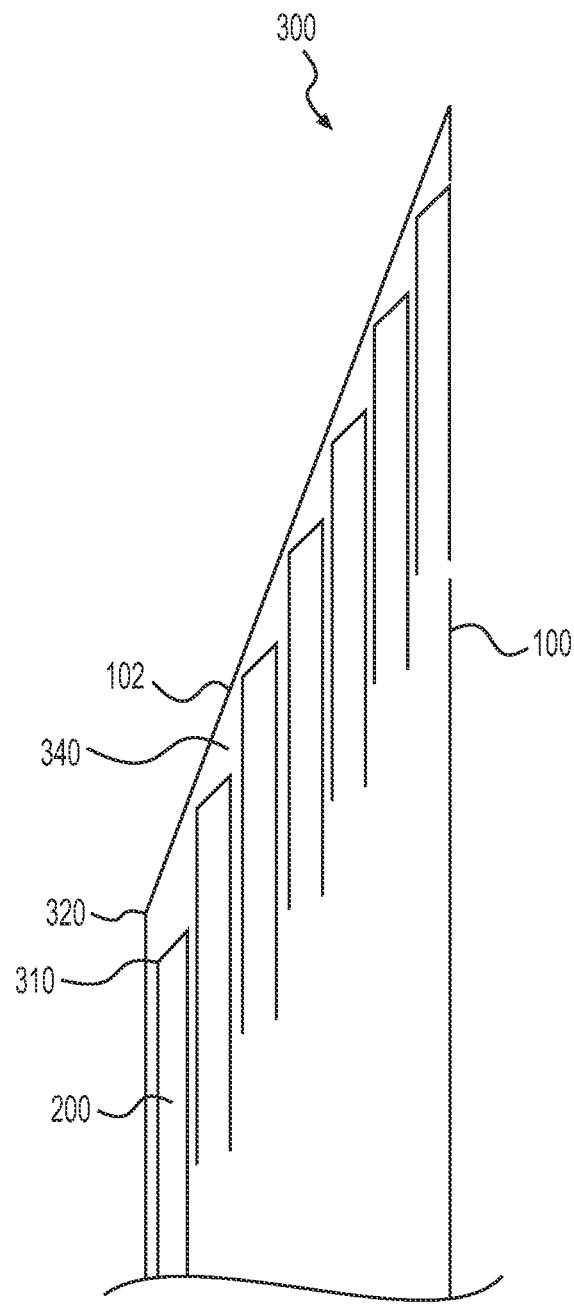

FIGS. 3A-3B illustrate a urine sensing probe 300 with plural optical 200 fibers positioned in a needle 100. The optical fibers preferably have a combined width of 1,000 microns or equal to the inside diameter of the needle. In FIG. 3A, there are two optical fibers 200 each with a width of 500 microns positioned in the needle 100. In FIG. 3B, multiple optical fibers 200 are positioned in the needle 100. In one embodiment, the plural optical fibers 200 extend between, and preferably from, distal and proximal ends of the needle 100.

Moreover, FIGS. 3A-3B illustrates a forward emitting optical fiber. As shown in FIG. 3A, an edge 310 of the fiber is located proximate to the beveled section 102 of the needle 100 oriented towards a first lateral side 330 thereof. Preferably, the edge 310 is positioned flush to the beveled section 102 of the needle 100. In one embodiment as illustrated in FIG. 3A, the edge 310 is positioned above an edge 320 of the needle located proximate to the beveled section 102. In another embodiment as illustrated in FIG. 3B, an edge of an optical fiber may be positioned above or below an edge 320 of the needle 100. In both FIGS. 3A-3B, there is the potential for adding clear or scattering fill 340 in an area between distal ends of optical fibers 200 and the beveled section 102. The scattering fill 340 advantageously may reduce the risk of tissue coring. The scattering fill 340 helps redirect excitation light from the fiber in a direction more towards the lateral direction. This increases the brightness level of excitation energy received by the sample, e.g., urine or tissue near the beveled surface. Moreover, the optical scattering fill with redirect emissions from the urine caused by the excitation into the optical fibers.

Figure 3C:
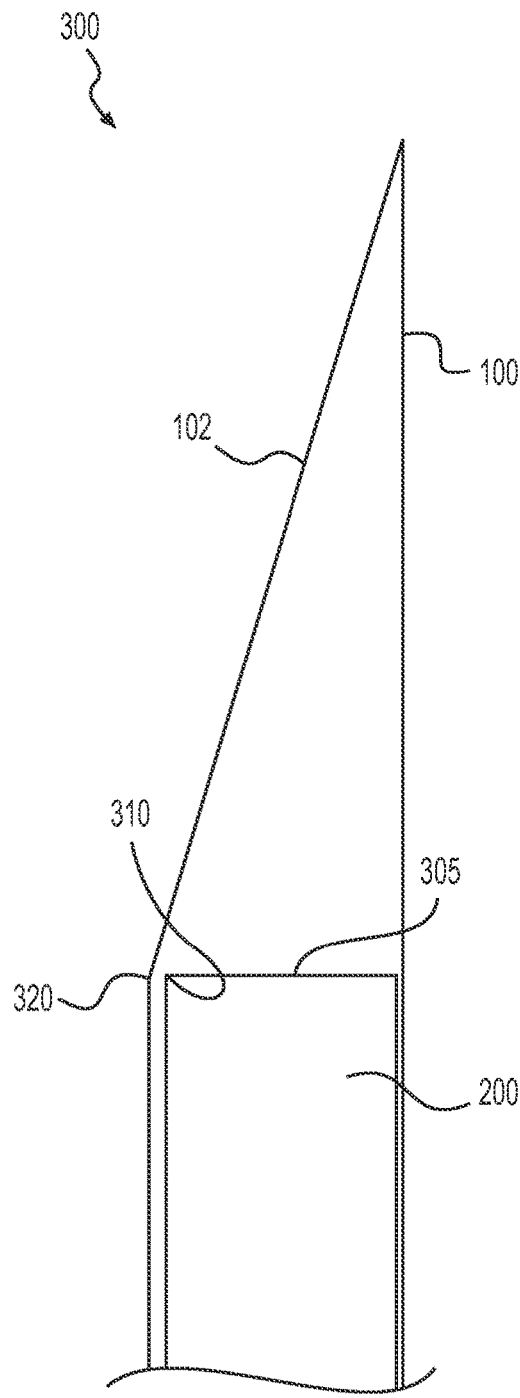
Figure 3D:
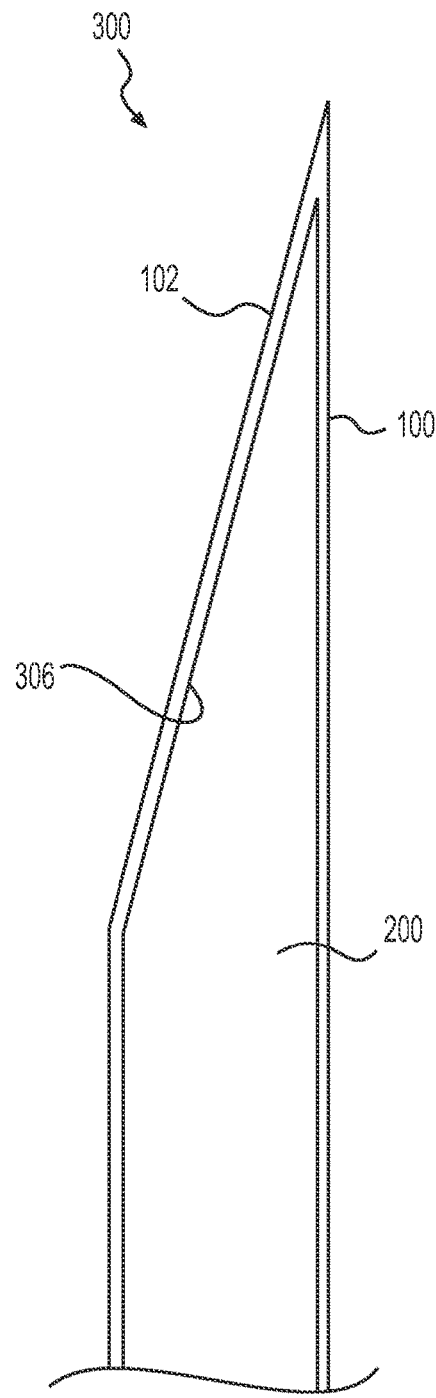
Figure 3E:
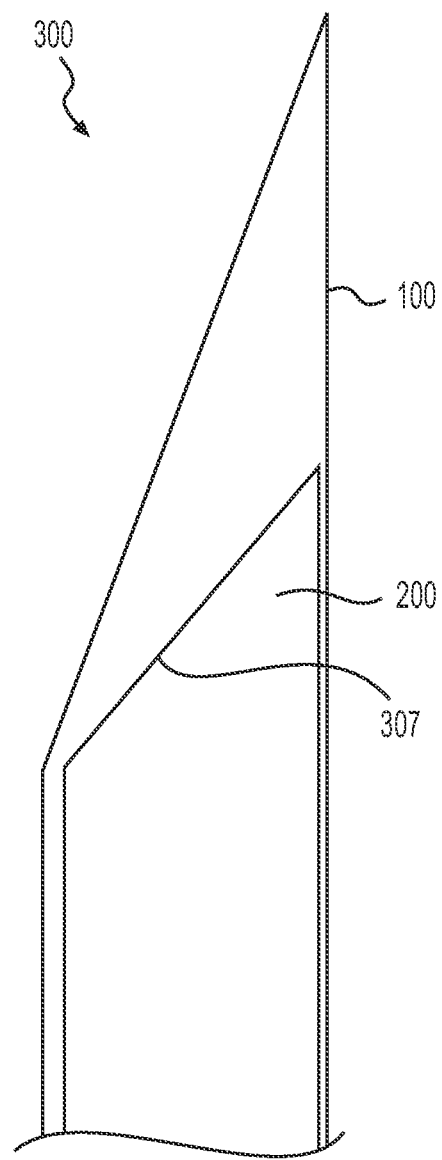

Meanwhile, FIGS. 3C, 3D and 3E illustrate a urine sensing probe 300 with a single optical fiber 200 positioned in the needle 100. FIG. 3C illustrates the needle 100 having a 22° beveled section 102. The beveled section 102 may however be any angle as envisaged for the needle. The single optical fiber 200 has an end 305 that is polished to about 90° with respect to the vertical axis of the needle 100. It is understood that the optical signal is maximum at an angle of 90° with respect to the vertical axis of the the needle.

FIG. 3D illustrates an end 306 of the single optical fiber 200 polished to about 22° with respect to the vertical axis of the needle 100. The polished end 306 is substantially flush to the beveled section 102 of the needle 100. In one embodiment, the entire polished end 306 of the optical fiber 200 is substantially proximate to the beveled section 102 of the needle 100. It is understood that the gap or space existing between the optical fiber and beveled edge of the needle, e.g., cutting edge, may cause tissue coring. However, the optical signal diminishes as the angle decreases, and eventually the optical signal would become nearly zero at the critical angle where total internal reflection in the fiber prevents the light from exiting or entering the fiber.

Moreover, FIG. 3E illustrates a single optical fiber 200 having an end 307 polished to about 45° with respect to the vertical axis of the needle 100. Based upon the above-mentioned embodiments, it is envisaged that a balance must be struck between avoiding total internal reflection and tissue coring.

According to another embodiment, the optical fiber 200 at a distal end is polished as shown in FIGS. 2 and 3A-E. Preferably, as shown in FIG. 2, it is polished between about 90° and 20° with respect to the vertical axis of the needle. Namely, the distal facet may be polished such that is ranges between 20° and 89°, 88°, 87°, 86°, 85°, 84°, 83°, 82°, 81°, 80°, 79°, 78°, 77°, 76°, 75°, 74°, 73°, 72°, 71°, 70°, 69°, 68°, 67°, 66°, 65°, 64°, 63°, 62°, 61°, 60°, 59°, 58°, 57°, 56°, 55°, 54°, 53°, 52°, 51°, 50°, 49°, 48°, 47°, 46°, 45°, 44°, 43°, 42°, 41°, 40°, 39°, 38°, 37°, 36°, 35°, 34°, 33°, 32°, 31°, 30°, 29°, 28°, 27°, 26°, 25°, 24°, 23°, 22° and 21° with respect to the vertical axis of the needle. With respect to the above-mentioned embodiment, they advantageously provide higher optical collection efficiency and less back-reflection of excitation light when the angle of the fiber polished surface is larger, and is maximized when the angle equals 90°. On the other hand, the embodiments advantageously provide relief from tissue coring when the angle with respect to the vertical axis of the needle is closer to that of the beveled surface of the needle. It is optimized when the angle equals 22°.

FIGS. 4A-4B illustrate alternative views of the embodiment shown in FIG. 3A. Namely, two optical fibers 200 are depicted in the needle 100 each have varying lengths configured to extend from proximal end 100a of the needle 100 to the beveled section 102. The optical fibers preferably do not extend beyond the beveled section 102.

Figure 5:
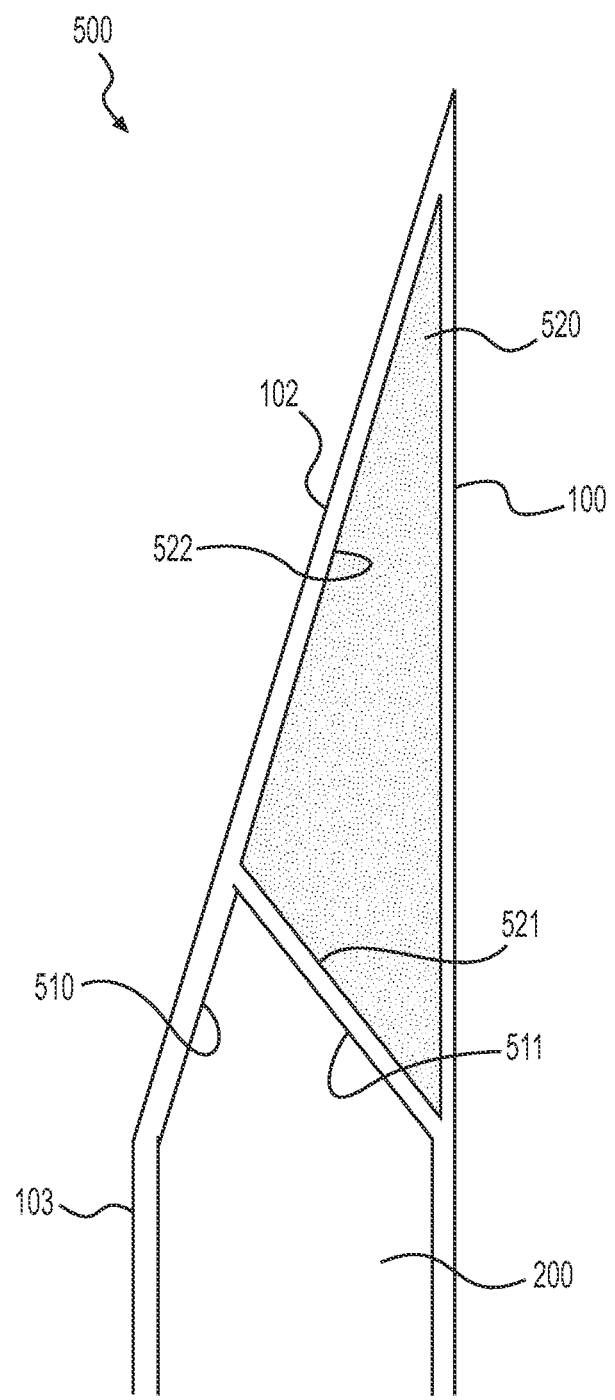
FIG. 5 illustrates optical fibers housed in a needle according to another embodiment of the present application.

According to another embodiment, a urine sensing probe 500 includes a needle 100 with a single optical fiber 200 located therein as shown in FIG. 5. In this figure, the optical fiber 200 has a first distal surface 510 that is polished such that it is proximate to the beveled distal section 102 and oriented towards the first lateral side 103 of the needle 100. Preferably, the distal surface 510 is positioned substantially flush to the beveled distal section 102. Namely, the distal surface 510 of the optical fiber 200 is polished to conform to an area of the beveled distal section 102 such that light exits and returns through the side of the optical fiber 200. This embodiment advantageously provides the probe with a lateral looking orientation enabling the sensing of urine in vessels which are penetrated through a side wall. The single optical fiber 200 may be employed as a conduit for both transmitting excitation light ultimately to urine and receiving emission characteristics based thereon. The single optical fiber may be mechanically bifurcated in order to communicate with ports, e.g., optical connectors, for an emission sensor and excitation source. Alternatively, the light going to and coming from the single optical fiber will be separated into excitation light and emission light by using a dichroic beam splitter. Dichroic beam splitters are well known in the industry. Generally, they are a thin film interference filter selected so that excitation wavelengths will pass through the filter when it is oriented at 45° to the excitation beam, and is focused into the fiber. Emission light at a longer wavelength on the return path will reflect off of the filter and be directed at 90° to its direction and be focused on the detector.

In a further embodiment, the urine sensing probe 500 also includes a solid reflector 520. The solid reflector 520 is positioned such that a lower surface 521 thereof is proximate to a second distal surface 511 of the optical fiber 200. Moreover, the reflector 520 is positioned, either via welding or adhesive, inside an inner body of the needle 100. In an exemplary embodiment, the lower surface 521 is parallel to the second distal surface 511. In another exemplary embodiment, the beveled distal section 102 is substantially parallel to, and substantially equivalent in length to, the length based upon the sum of the distal surface 510 of the optical fiber 200 and a side surface 522 of the reflector 520. Preferably, side surface 522 is about 22° with respect to a vertical axis of the needle. This embodiment advantageously increases the optical collection efficiency of the fiber sensor without causing an increased risk of coring the tissue. The extra optical collection efficiency is a result of the excitation light directed from the lower reflector surface 521 out of the fiber through surface 510 and the collection of emitted light in the reverse direction through surface 510 and reflected off the lower reflector surface 521 down the fiber to a detector.

Figure 6A:
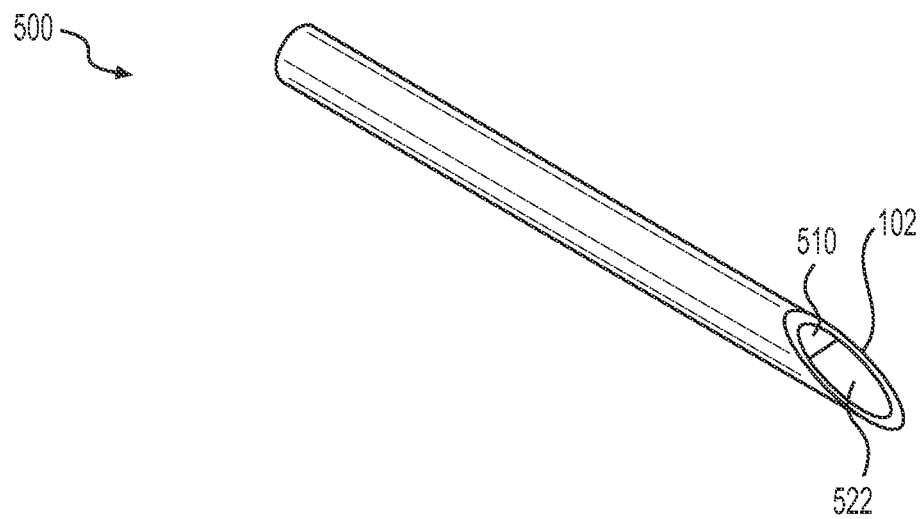
FIGS. 6A-C illustrate alternative views of FIG. 5.
Figure 6B:
Figure 6C:
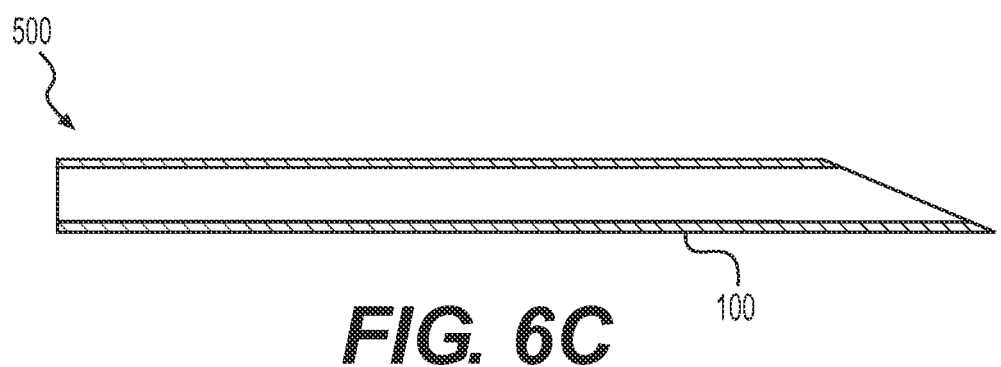

FIGS. 6A-C illustrate alternative views of the urine sensing probe 500 of FIG. 5. For example, FIG. 6A illustrates a top view of the probe 500 wherein the beveled distal section 102 is substantially aligned with the distal surface 510 of the optical fiber 200 and a side surface 522 of the reflector. FIG. 6B is a side view of the needle 100 and FIG. 6C is a side view illustrating a coreless tubular body of the needle 100.

According to another aspect of the application, a system 700 is disclosed for detecting urine as illustrated in FIG. 7. The system 700 include an urine sensing probe (not shown) as discussed above. The system also includes a user interface 710 configured to transmit excitation light through the optical fiber of the urine sensing probe. The user interface 710 may also be configured to detect an emission from urine which has been excited by light. In an exemplary embodiment, the user interface 710 is a single device including an excitation source and an emission sensor. The user interface 710 may include one or more ports. The number of optical fibers may be less than, equal to, or greater than the number of ports available on the user interface with at least one port being present. If there is a single port on the user interface 710, a beam splitter configured to transmit the appropriate signals to the emission sensor and from the excitation source, respectively may be employed.

Alternatively, FIG. 7 shows two ports 711, 712 on the user interface 710. One of the ports 711 may be dedicated to transmitting a wavelength of light, preferably ranging from about 200-450 nm, and more preferably 360-405 nm, ultimately to urine. Another port 712 is primarily dedicated to receiving and detecting a spectral emission based upon the urine excited by a wavelength of light. If the urine sensing probe includes a single optical fiber, the fiber is bifurcated at its distal end to mate with ports 711, 712 of the user interface. If two optical fibers 200 are employed, mechanical bifurcation is not required.

Figures 8A, 8B:
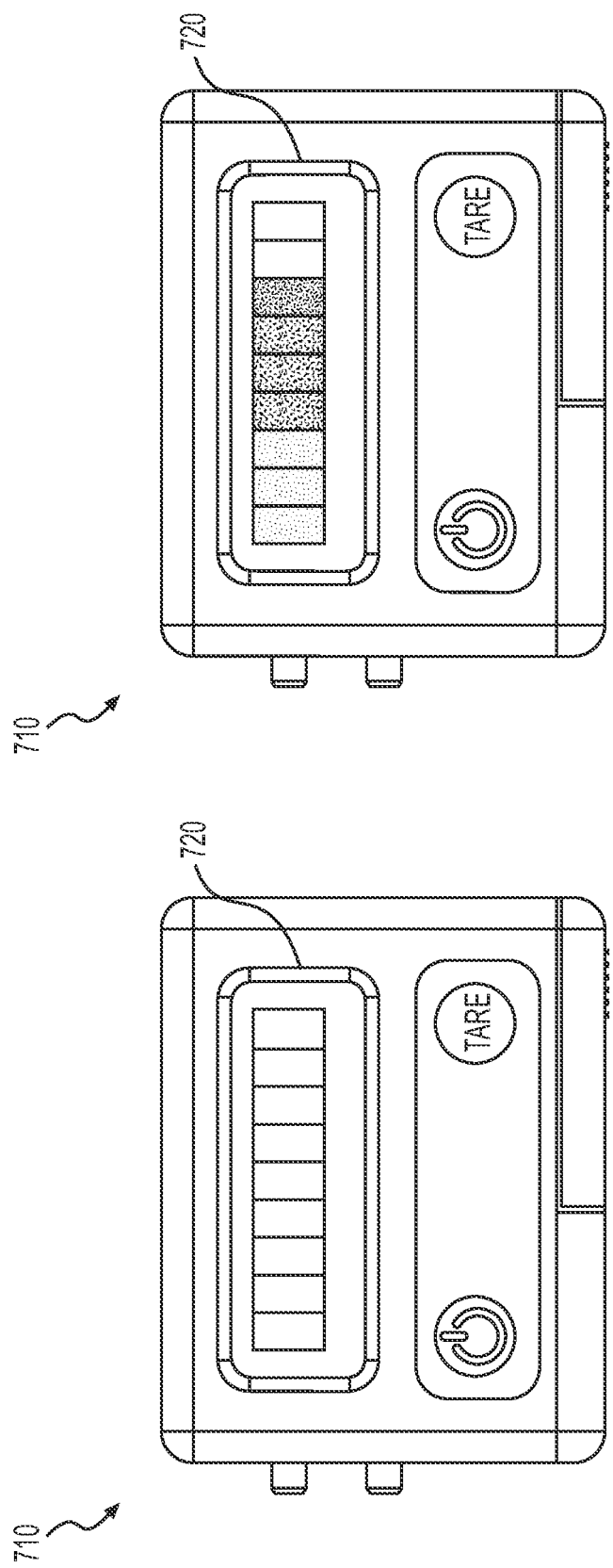
FIGS. 8A-8B illustrate a user interface employed in the system of FIG. 7 for transmitting excitation light and detecting fluorescence characteristics in urine according to an embodiment of the present application.

According to another embodiment, the extension fiber 210 extending from the mechanically robust section 202 of an optical fiber is connected with the the user interface 710. The user interface 700 may include a graphical display 720 capable of indicating the proximity of the system 700 to urine located inside a patient's body. As shown in FIGS. 8A-B, the graphical display 720 may include bars indicating proximity to a urine source. FIG. 8A is turned off, e.g., no bars illuminated, while FIG. 8B is turned on. The bars may be colored, for example in red, yellow and green to show intensity. Any indicator though may be employed as commonly known in the art which is visible to the clinician.

In another embodiment, the user interface 700 may also include a power on/off button. This allows the user interface to be shut down when not in use. The user interface 710 may also include a reset or tare button feature in order to calibrate the probe.

According to a further embodiment, the user interface 710 may be battery powered. This allows a clinician to transport the user interface 710 without being constrained by static power sources, e.g., power outlet. Alternatively, the user interface 710 is powered by a static electrical source.

The system 700 may also include an audio device that is operably coupled to the emission fluorescence sensor. The audio device may be separate from, or integrated with, the user interface 710. The audio device is capable of providing sounds which vary in volume, pitch or temporal pattern based upon urine fluorescence signal intensity. In one embodiment, the audio device may include an alarming mechanism which is set off by the signal exceeding a predetermined threshold.

Figure 9A:
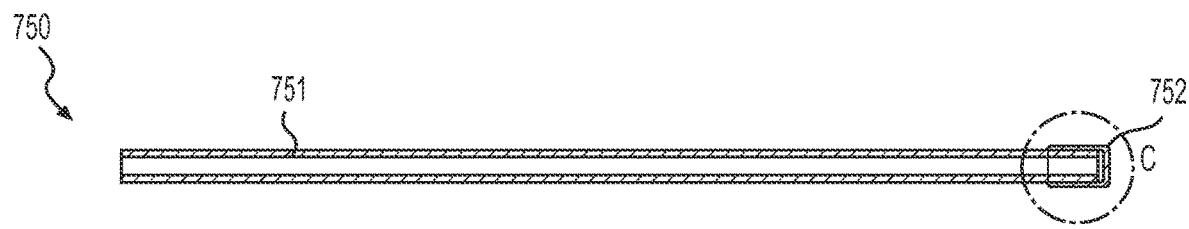
FIGS. 9A-C illustrate a calibration device employed in the system of FIG. 7 for calibrating a urine sensing probe prior to application according to an embodiment of the present application.
Figure 9B:
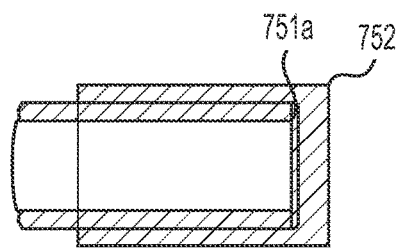
Figure 9C:

In yet another aspect of the application, the system 700 for detecting urine may also include a calibrating device 750 as shown in FIG. 7 and FIGS. 9A-9C. As shown in FIG. 9A, the calibrating device 750 may include a safety sheath 751 and a cap 752. The safety sheath 751 is not limited to any specific material. Moreover, the size of the safety sheath 751 is configured to house the urine sensing probe. As illustrated in FIG. 9B, the cap 752 is configured to cover a distal end 751a of the safety sheath. FIG. 9B is a five-times magnified view (5×) of FIG. 9A. FIG. 9C is a view of the inner tubular area of the safety sheath 751.

Moreover a coating of a fluorescent compound(s) with similar excitation and emission characteristics to urine is applied to an inner surface of the cap 752. In one embodiment the coating is nicotinamide adenine dinucleotide NADPH, flavin adenine dinucleotide (FAD). In a preferred embodiment the fluorescent compound is contained in a polymer or other clear matrix that renders it stable in fluorescence intensity and suitable as a fluorescence intensity standard, The fluorescent coating assists with calibrating the urine sensing probe to optimally set detection signal levels of urine within the body. Namely, the fluorescent coating replicates the fluoroescence characteristics of pure urine. During calibration, the clinician ensures that the safety sheath 751 and cap 752 are covering the urine sensing probe. Then, the clinician presses the Tare button on the user interface to clear previous data and optimize to sensitivity of the sensing probe. The calibrating device 750 is removed during intervention of the needle toward the renal saddle.

In another embodiment, the system in FIG. 7 is configured to display concentration of fluorophores. The concentration is determined from the urine emission signal strength and is calibrated by comparison to solutions with known concentrations. In a further embodiment the system has several optical filters or beam splitters and two or more detectors. Each detector looks at a different wavelength band that corresponds to the emitted wavelengths from different fluorophores. The embodiment is advantageous for reporting the ratio between the concentrations of different fluorophores that may indicate disease states such as cancer.

Figure 10:
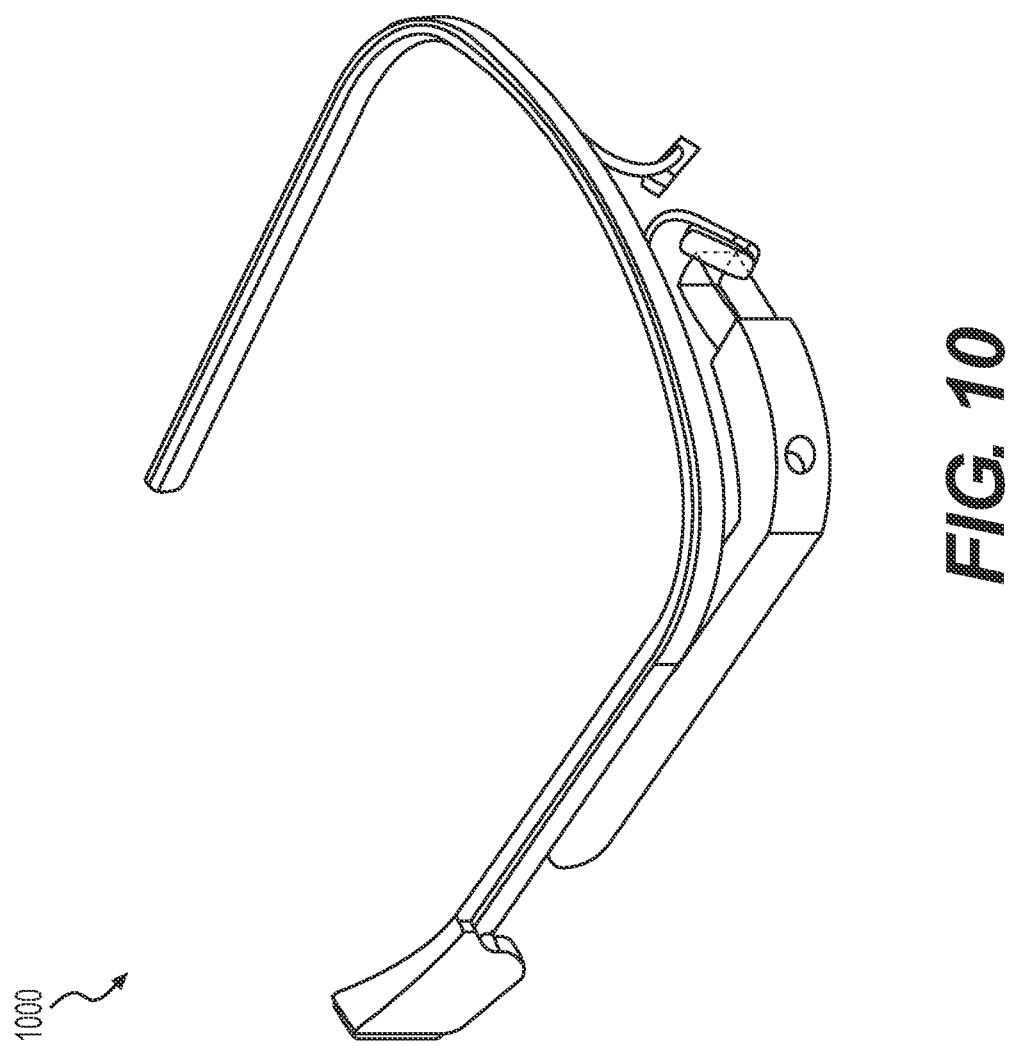
FIG. 10 illustrates a remote user according to an embodiment of the present application.

According to another embodiment, the system may further comprise a wireless interface to a remote user interface or a recording device 1000 as shown in FIG. 10. In an exemplary embodiment, the remote user interface 1000 may include wearable technology. For example, the wearable technology may be a heads-up display. As as shown in FIG. 10, the remote user interface 1000 are smart glasses, such as for example Google glass. The wearable technology may also be any device envisaged within the capability of skilled artisan that is lightweight. By so doing, the clinician's hands are available to perform other functions.

Figure 11:
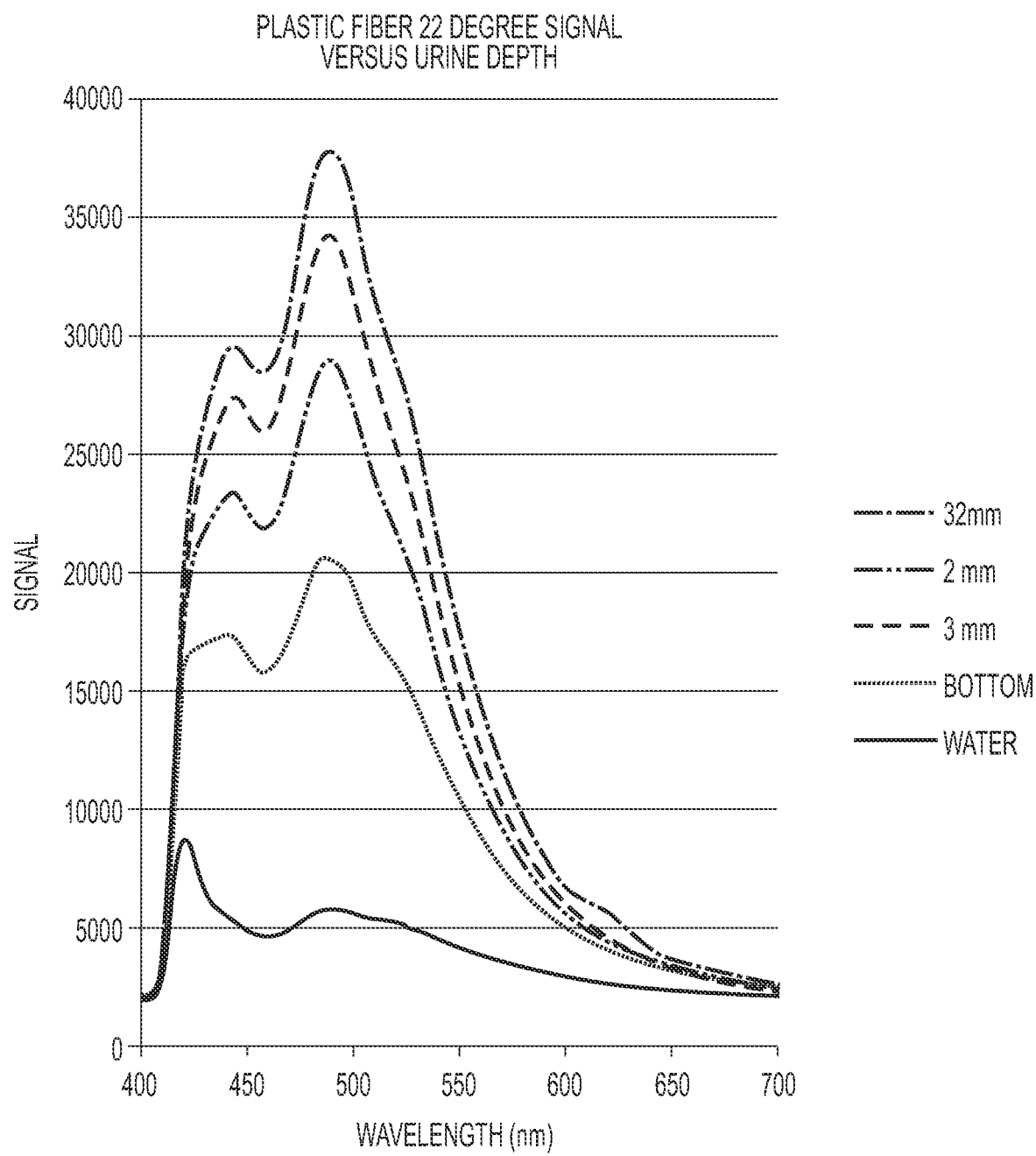
FIG. 11 illustrates graphical data of signal strength versus urine depth in-vivo.

In even a further embodiment of the system, a method of determining the depth of urine from the signal strength is described. The unique optical properties of the fiber sensors cause an increase in signal when the sensor is immersed in an increasing depth of urine. This advantageous embodiment is illustrated in FIG. 11. The signal increases from an initial reading of about 20,000 when the probe is touching the bottom surface. It increases to around 28,000 when it is raised to 2 mm above the bottom surface. It increased to around 33,000 when it is 3 mm above the bottom surface. The increase become less pronounced further from the bottom surface. This embodiment is advantageous in detecting the difference between trace amounts of urine and volumes of urine with spatial scales of several mm to 32 mm.

Figure 12A:
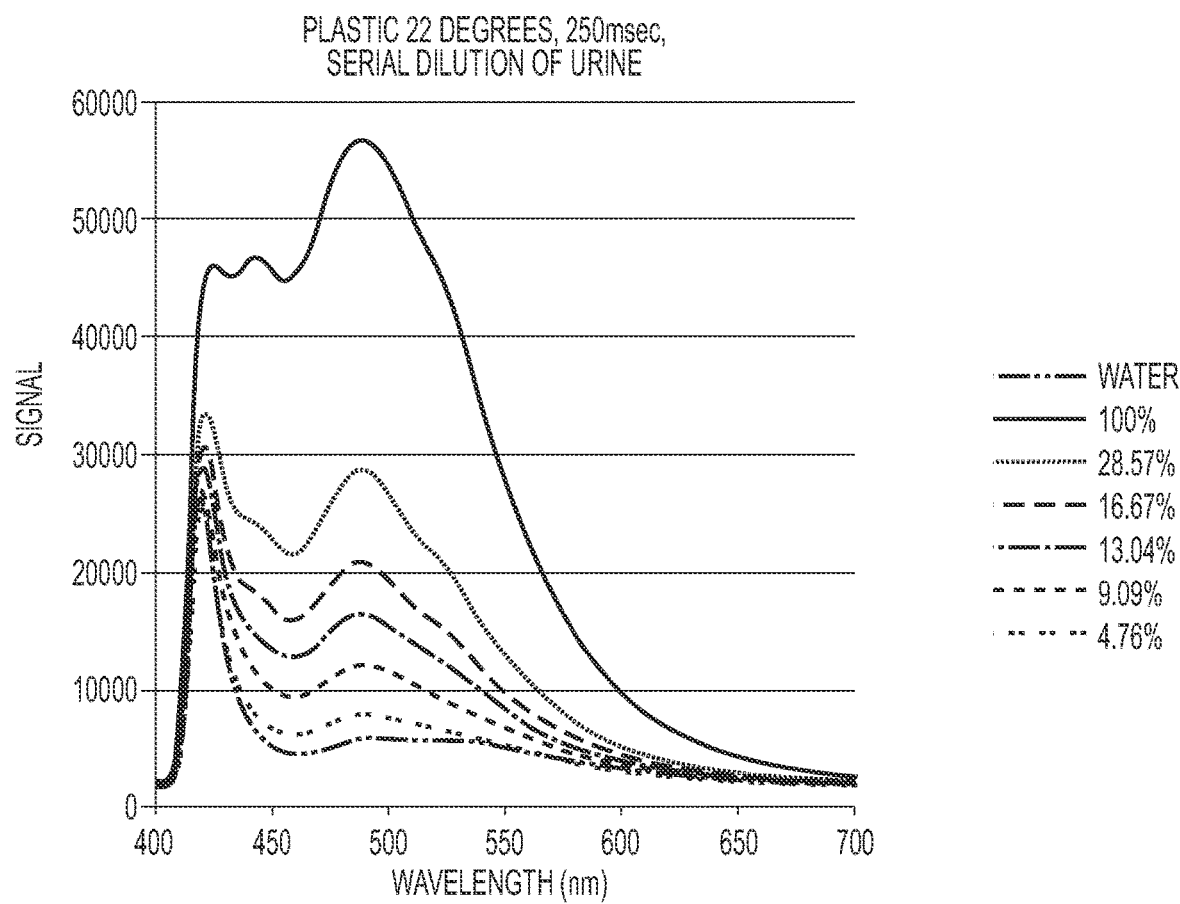
FIGS. 12A-B illustrate graphical data of signal strength versus urine concentration at a predetermined depth in-vivo.
Figure 12B:
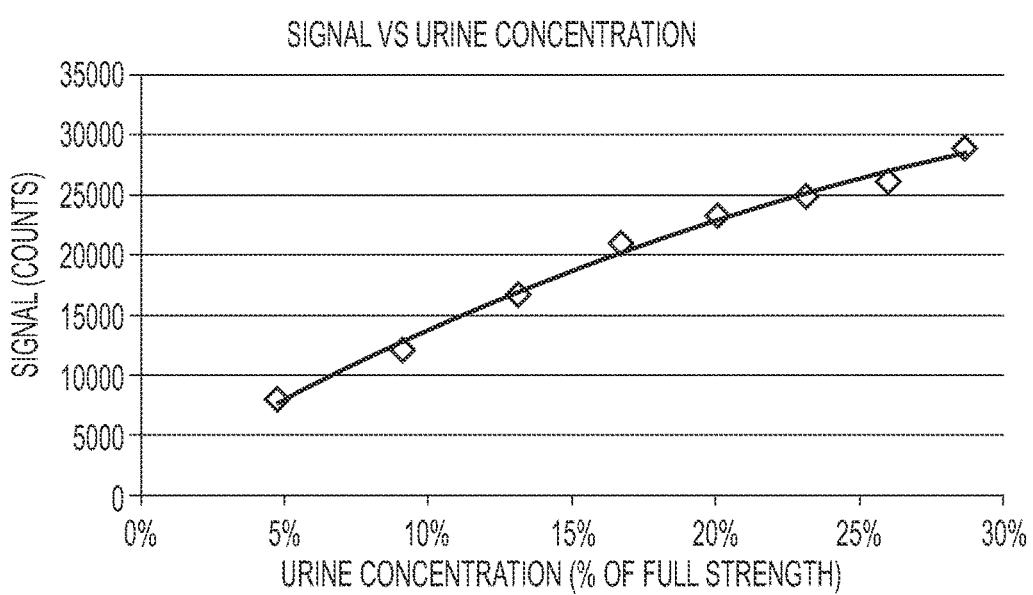

In another aspect of the application, there is a method of employing the sensor probe to measure concentration of one or more fluorophores in urine. These fluorophores may include but are not limited to NADH, NADPH, flavoproteins and porphyrins. For a fixed depth of urine, signal strength increases in a substantially linear manner with concentration. As shown in FIGS. 12A and 12B, the signal of full strength urine and urine mixed with various portions of water is shown to be proportional to the percentage of urine in the sample. This embodiment is advantageous for detecting concentration of fluorophores in urine in-vivo that have physiological meaning to a clinician. In one embodiment these fluorophores provide an indication of cancerous tissue metabolism. This may be based upon a comparison with normal urine. Moreover, flavoproteins and poryfrins have been shown to be associated with patients with cancers. In a preferred embodiment for detecting cancers, the wavelengths of detection are selected to optimize the signal for flavoproteins and porphryins.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A urine sensing probe comprising:
a needle having a tubular portion, a proximal end, a distal end, and a beveled distal section oriented towards a first lateral side of the needle;
an optical fiber positioned in the needle, the optical fiber having a distal surface proximate to the beveled distal section and oriented towards the first lateral side, a portion of the distal surface being substantially parallel to the beveled distal section, the distal surface being configured to emit and/or collect light through the beveled distal section; and
a member distal of the distal surface of the optical fiber configured to redirect light between the first lateral side of the needle and the distal surface of the optical fiber.

2. The urine sensing probe of claim 1, wherein the member comprises a solid reflector positioned between the distal surface of the optical fiber and the distal end of the needle.

3. The urine sensing probe of claim 2, wherein the solid reflector includes a surface that is substantially parallel to a second surface of the optical fiber and oriented about 45 degrees with respect to the longitudinal axis of the needle.

4. The urine sensing probe of claim 2, wherein the optical fiber is configured such that light is emitted from an area of the first lateral side of the needle disposed below the solid reflector.

5. The urine sensing probe of claim 1, wherein the member comprises a scattering fill positioned between the distal surface of the optical fiber and the distal end of the needle.

6. A system for detecting urine comprising:
the urine sensing probe of claim 1;
a source for transmitting excitation energy through the urine sensing probe towards urine; and
a detector for detecting fluorescence in urine through the urine sensing probe.

7. The system of claim 6, wherein the excitation energy includes UV-VIS light having a wavelength ranging between about 250-450 nm.

8. The system of claim 6, further comprising
a graphical display connected to the detector.

9. The system of claim 6, further comprising
an audio device connected to the detector.

10. The system of claim 6, further comprising
a wireless display connected to the detector from a remote location.

11. The system of claim 6, further comprising
a calibration material having a spectrum similar to a urine fluorescence condition employed by the detector.

12. The system of claim 6, wherein the member comprises a solid reflector positioned between the distal surface of the optical fiber and the distal end of the needle, and the solid reflector includes a surface that is substantially parallel to a second surface of the optical fiber and oriented about 45 degrees with respect to the longitudinal axis of the needle.

13. The system of claim 6, wherein the member comprises a solid reflector positioned between the distal surface of the optical fiber and the distal end of the needle, and the optical fiber is configured such that light is emitted from an area of the first lateral side of the needle disposed below the solid reflector.

14. A method of determining concentration of urine in-vivo comprising:
providing the urine sensing probe according to claim 1;
introducing the urine sensing probe in-vivo to a predetermined depth;
transmitting excitation light through the urine sensing probe toward the urine;
detecting signal strength of an emission wavelength of a fluorophore present in the urine; and
determining the concentration of the urine based upon the signal strength.

15. The method of claim 14, further comprising:
comparing the determined concentration of urine with a standard concentration of urine at the predetermined depth to assess risks for cancer.

16. The method of claim 14, further comprising reflecting light with a solid reflector having a surface that is substantially parallel to a second surface of the optical fiber and oriented about 45 degrees with respect to the longitudinal axis of the needle.

17. The method of claim 14, wherein the optical fiber is configured such that light is emitted from an area of the first lateral side of the needle disposed below the solid reflector.

18. A method of determining depth of urine in a cavity or lumen in-vivo comprising:
providing the urine sensing probe according to claim 1;
introducing the urine sensing probe into the cavity or lumen;
transmitting excitation light through the urine sensing probe toward the urine;
detecting a signal strength of an emission wavelength of a fluorophore present in the urine; and
determining the depth of the urine in the cavity or lumen based upon the signal strength.

19. The method of claim 18, further comprising reflecting light with a solid reflector having a surface that is substantially parallel to a second surface of the optical fiber and oriented about 45 degrees with respect to the longitudinal axis of the needle.

20. The method of claim 18, wherein the optical fiber is configured such that light is emitted from an area of the first lateral side of the needle disposed below a solid reflector.

* * * * *